United States Patent
Wu et al.

(10) Patent No.: US 11,702,400 B2
(45) Date of Patent: Jul. 18, 2023

(54) SALT TYPES, CRYSTAL FORMS, AND PREPARATION METHODS FOR BENZOPYRAZOLE COMPOUNDS AS RHO KINASE INHIBITORS

(71) Applicant: MEDSHINE DISCOVERY INC., Jiangsu (CN)

(72) Inventors: Lingyun Wu, Shanghai (CN); Zheming Xiao, Shanghai (CN); Chunyan Jiang, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/767,104

(22) PCT Filed: Oct. 16, 2020

(86) PCT No.: PCT/CN2020/121388
§ 371 (c)(1),
(2) Date: Apr. 7, 2022

(87) PCT Pub. No.: WO2021/073592
PCT Pub. Date: Apr. 22, 2021

(65) Prior Publication Data
US 2022/0380336 A1     Dec. 1, 2022

(30) Foreign Application Priority Data
Oct. 18, 2019   (CN) .......................... 201910993446.1

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; C07D 401/02
USPC ....................................................... 546/275.7
See application file for complete search history.

(56) References Cited

U.S. PATENT DOCUMENTS

| | | | |
|---|---|---|---|
| 11,345,678 B2 * | 5/2022 | Wu | ....................... C07D 403/12 |
| 2011/0034441 A1 | 2/2011 | Hood et al. | |
| 2017/0226105 A1 | 8/2017 | Hu et al. | |
| 2021/0371393 A1 | 12/2021 | Wu et al. | |

FOREIGN PATENT DOCUMENTS

| | | |
|---|---|---|
| CN | 102595899 A | 7/2012 |
| CN | 107108581 A | 8/2017 |
| WO | 2005074643 A2 | 8/2005 |
| WO | 2006105081 A2 | 10/2006 |
| WO | 2008054599 A2 | 5/2008 |
| WO | 2010104851 A1 | 9/2010 |
| WO | 2013028445 A1 | 2/2013 |
| WO | 2013045413 A1 | 4/2013 |
| WO | 2014055996 A2 | 4/2014 |
| WO | 2014134388 A1 | 9/2014 |
| WO | 2016028971 A1 | 2/2016 |
| WO | 2016188481 A1 | 12/2016 |
| WO | 2019201297 A1 | 10/2019 |

OTHER PUBLICATIONS

Jan. 18, 2021 International Search Report issued in International Patent Application No. PCT/CN2020/121388.
Jan. 18, 2021 Written Opinion of the International Searching Authority issued in International Patent Application No. PCT/CN2020/121388.
Extended European Search Report dated Jun. 20, 2022 issued in European Patent Application No. 20876972.9.
Nov. 1, 2022 Japanese First Office Action issued in Japanese Patent Application No. 2022-523071.

* cited by examiner

*Primary Examiner* — Charanjit Aulakh
(74) *Attorney, Agent, or Firm* — Houston Beshining Law Office PLLC; Liangang Ye

(57) ABSTRACT

Salt types, crystal forms, and preparation methods for benzopyrazole compounds as RHO kinase inhibitors. Specifically, disclosed are hydrochloride and acetate of compounds of formula (I) and crystal forms thereof, as well as application of the salt types and the crystal forms in preparation of RHO inhibitor drugs.

(I)

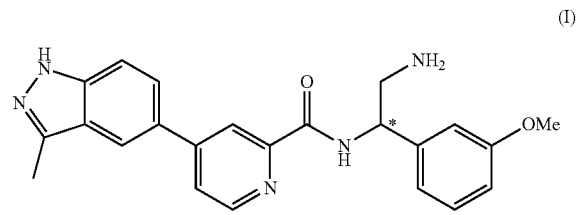

13 Claims, 5 Drawing Sheets

SALT TYPES, CRYSTAL FORMS, AND PREPARATION METHODS FOR BENZOPYRAZOLE COMPOUNDS AS RHO KINASE INHIBITORS

The present application is a National Stage of International Application No. PCT/CN2020/121388, filed on Oct. 16, 2020, which claims priority of the Chinese Patent Application No. CN201910993446.1 filed on Oct. 18, 2019, the contents of which are incorporated herein by reference in their entireties.

TECHNICAL FIELD

The present disclosure relates to a salt type, a crystal form and a preparation method thereof for benzopyrazole compounds as RHO kinase inhibitors, specifically relates to a hydrochloride and an acetate of a compound of formula (I), and a crystal form thereof, and also includes a use of the salt type and crystal form in the manufacture of RHO inhibitor medicaments.

BACKGROUND

RHO associated kinase (abbreviated as ROCK), a serine/threonine protein kinase, is a downstream target effector molecule of RHO and is widely expressed in human body. RHO associated kinase (ROCK) is involved in the regulation of myosin light chain (MLC) and is suitable for vasodilatory therapy. New research supports the involvement of ROCK kinase in the regulation of immune response and fibroblast activation in TH17 cells, which may extend the indications for pulmonary diseases such as pulmonary fibrosis and asthma, and further indications include autoimmune diseases. ROCK kinase family includes two subtypes, ROCK1 and ROCK2. ROCK2 kinase is related to inflammation and fibrosis. Selective ROCK2 inhibitor does not cause vasodilation at high concentration in vitro vasodilation experiment, which can reduce cardiovascular side effects. Although the embryo mortality rate of ROCK1 knockout mice is not high, most of them die from cytoskeleton variation caused by MLC phosphorylation reduction after birth, while 90% of ROCK2 knockout mice die in embryonic stage, but there is no difference between surviving mice and wild type mice, so selective inhibition of ROCK2 activity may have higher safety. Therefore, selective ROCK2 kinase inhibitors can avoid cardiovascular side effects of drugs.

KD025 (WO2006105081A1, WO2008054599A1, WO2010104851A1 and WO2014055996A1) is an oral selective inhibitor of ROCK2 kinase developed by Kadmon Company. Studies have shown that KD025 represents a novel mechanism to treat idiopathic pulmonary fibrosis (IPF) by inhibiting fibrosis-regulating proteins such as RHO kinase. The trigger for idiopathic pulmonary fibrosis (IPF) may be muscle damage. The body response to injury involves the reorganization of the actin cytoskeleton in a variety of cells (e.g., epithelial cells, fibroblasts, endothelial cells, and macrophages), while the assembly of actin filaments and the contraction of actomyosins are regulated by RHO kinase family proteins (including ROCK1 and ROCK2) guidance. Previous studies have shown that RHO kinase family proteins can be activated in the lungs of IPF patients and animal models of this disease, and RHO kinase inhibitors can prevent the tissue fibrosis process in these models and induce the established fibrosis to subside. At present, the Phase II clinical trial of moderate to severe psoriasis has been completed, and KD025 is in the Phase II clinical research stage of idiopathic pulmonary fibrosis (IPF) treatment.

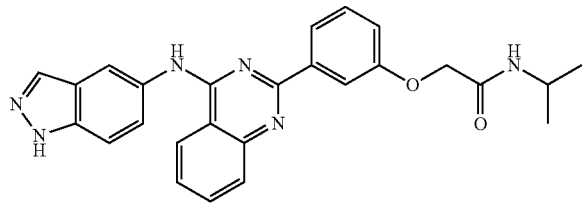

KD-025

WO2014134388A1 and WO2016028971A1 also disclose a class of compounds with structural general formula as shown in formula (a) and formula (b), which can also be used in the treatment of cardiovascular diseases, neuropathological diseases, tumors, autoimmune diseases, pulmonary fibrosis, inflammatory diseases, etc.

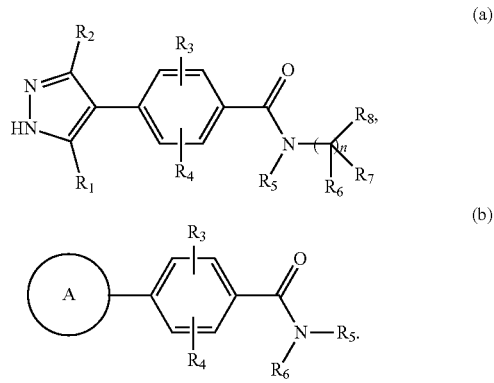

Content of the Present Invention

The present disclosure provides a hydrochloride of a compound of formula (I), having the structure shown in formula (I')

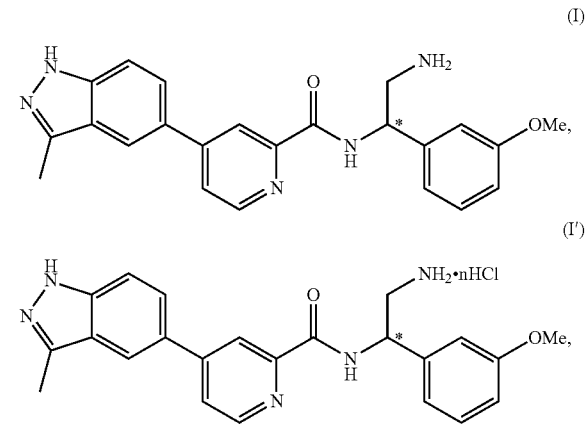

wherein, n is 1.6-2.4, and the carbon atoms with "*" are chiral carbon atoms, which exist in a (R) or (S) single enantiomer form or a (R) or (S) single enantiomer-rich form.

In some embodiments of the present disclosure, the n is 1.9, 2.0 or 2.1.

In some embodiments of the present disclosure, the hydrochloride has the structure shown in formula (I-1),

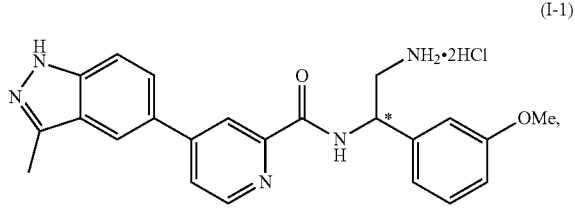

(I-1)

wherein, the carbon atom with "*" is a chiral carbon atom, which exists in a (R) or (S) single enantiomer form or a (R) or (S) single enantiomer-rich form.

In some embodiments of the present disclosure, the hydrochloride has the structure shown in formula (II-1),

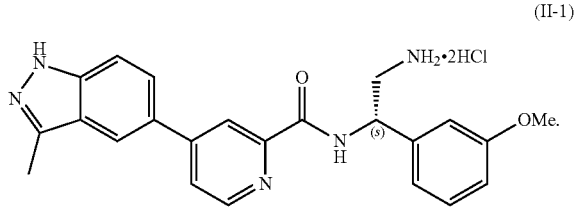

(II-1)

In some embodiments of the present disclosure, the X-ray powder diffraction (XRPD) pattern measured by Cu Kα radiation of a crystal form A of the hydrochloride has characteristic diffraction peaks at the following 2θ angles: 14.77±0.20°, 20.50±0.20°, 22.38±0.20° and 24.15±0.20°.

In some embodiments of the present disclosure, the X-ray powder diffraction pattern measured by Cu Kα radiation of the crystal form A of the hydrochloride has characteristic diffraction peaks at the following 2θ angles: 10.22±0.20°, 13.36±0.20°, 14.77±0.20°, 18.69±0.20°, 20.50±0.20°, 22.38±0.20°, 24.15±0.20°, and 25.03±0.20°.

In some embodiments of the present disclosure, the X-ray powder diffraction pattern measured by Cu Kα radiation of the crystal form A of the hydrochloride has characteristic diffraction peaks at the following 2θ angles: 7.38°, 9.32°, 10.22°, 13.36°, 14.77°, 15.21°, 18.69°, 20.50°, 21.69°, 22.08°, 22.38, 24.15°, 24.58°, 25.03°, 26.28°, 27.13°, 28.15°, 29.44°, 30.15°, 31.49°, 32.1°, 32.69°, 35.17°, and 38.51°.

In some embodiments of the present disclosure, the XRPD pattern of the crystal form A of the hydrochloride is shown in FIG. 1.

In some embodiments of the present disclosure, the peak positions and relative intensities of the diffraction peaks in the XRPD pattern measured by Cu Kα radiation of the crystal form A of the hydrochloride are shown in the following Table 1:

TABLE 1

XRPD diffraction data of the crystal form A of the compound of formula (II-1)

| No. | 2θ (°) | d-Spacing (Å) | Intensity | Relative intensity (%) |
|---|---|---|---|---|
| 1 | 7.38 | 11.98 | 287.96 | 13.08 |

TABLE 1-continued

XRPD diffraction data of the crystal form A of the compound of formula (II-1)

| No. | 2θ (°) | d-Spacing (Å) | Intensity | Relative intensity (%) |
|---|---|---|---|---|
| 2 | 9.32 | 9.49 | 204.84 | 9.3 |
| 3 | 10.22 | 8.66 | 559.92 | 25.43 |
| 4 | 13.36 | 6.63 | 628.24 | 28.53 |
| 5 | 14.77 | 6.00 | 1309.95 | 59.5 |
| 6 | 15.21 | 5.82 | 973.08 | 44.2 |
| 7 | 18.69 | 4.75 | 997.97 | 45.33 |
| 8 | 20.5 | 4.33 | 1228.56 | 55.8 |
| 9 | 21.69 | 4.10 | 360.44 | 16.37 |
| 10 | 22.08 | 4.03 | 886 | 40.24 |
| 11 | 22.38 | 3.97 | 2201.7 | 100 |
| 12 | 24.15 | 3.68 | 1367.01 | 62.09 |
| 13 | 24.58 | 3.62 | 459.56 | 20.87 |
| 14 | 25.03 | 3.56 | 894.6 | 40.63 |
| 15 | 26.28 | 3.39 | 554.27 | 25.17 |
| 16 | 27.13 | 3.29 | 382.63 | 17.38 |
| 17 | 28.15 | 3.17 | 603.64 | 27.42 |
| 18 | 29.44 | 3.03 | 606.61 | 27.55 |
| 19 | 30.15 | 2.96 | 322.57 | 14.65 |
| 20 | 31.49 | 2.84 | 209.76 | 9.53 |
| 21 | 32.1 | 2.79 | 106.48 | 4.84 |
| 22 | 32.69 | 2.74 | 126.86 | 5.76 |
| 23 | 35.17 | 2.55 | 216.88 | 9.85 |
| 24 | 38.51 | 2.34 | 154.39 | 7.01 |

In some embodiments of the present disclosure, the differential scanning calorimetry (DSC) curve of the crystal form A of the hydrochloride has an endothermic peak with an onset at 245.2° C.±3° C.

In some embodiments of the present disclosure, the DSC pattern of the crystal form A of the hydrochloride is shown in FIG. 2.

In some embodiments of the present disclosure, the thermogravimetric analysis (TGA) curve of the crystal form A of the hydrochloride has a weight loss of 3.14% occurred at 190.0° C.±3° C.

In some embodiments of the present disclosure, the TGA pattern of the crystal form A of the hydrochloride is shown in FIG. 3.

The present disclosure also provides a preparation method of the crystal form A of the hydrochloride, and the method comprises the following steps:

1) adding a compound of formula (I-1) to an organic solvent and stirring at an appropriate temperature;

2) filtering under reduced pressure, collecting filter cake;

3) vacuum drying the filter cake.

In some embodiments of the present disclosure, the organic solvent is ethanol in the preparation method of the crystal form A of the hydrochloride.

In some embodiments of the present disclosure, the appropriate temperature is 25° C. in the preparation method of the crystal form A of the hydrochloride.

In some aspects of the present disclosure, the stirring time is 10-12 hours in the preparation method of the crystal form A of the hydrochloride.

The present disclosure also provides an acetate of a compound of formula (I),

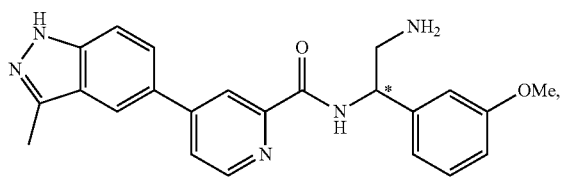

(I)

wherein, the carbon atom with "*" is a chiral carbon atom, which exists in a (R) or (S) single enantiomer form or a (R) or (S) single enantiomer-rich form.

In some embodiments of the present disclosure, the acetate has the structure shown in formula (I-2)

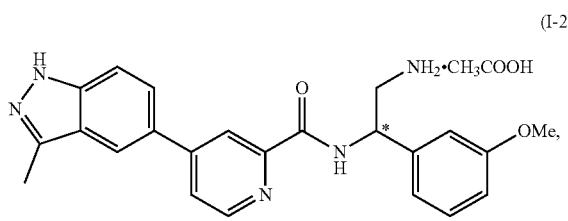

(I-2)

wherein, the carbon atom with "*" is a chiral carbon atom, which exists in a (R) or (S) single enantiomer form or a (R) or (S) single enantiomer-rich form.

In some embodiments of the present disclosure, the acetate has the structure shown in formula (II-2)

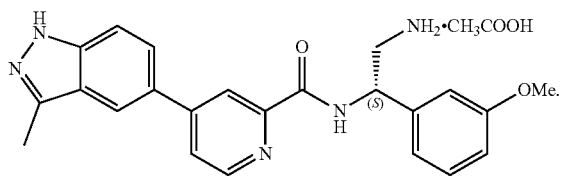

(II-2)

In some embodiments of the present disclosure, the X-ray powder diffraction pattern measured by Cu Kα radiation of a crystal form B of the acetate has characteristic diffraction peaks at the following 2θ angles: 6.18±0.20°, 12.37±0.20°, 17.08±0.20°, 21.22±0.20° and 24.88±0.20°.

In some embodiments of the present disclosure, the X-ray powder diffraction pattern measured by Cu Kα radiation of the crystal form B of the acetate has characteristic diffraction peaks at the following 2θ angles: 6.18±0.20°, 11.94±0.20°, 12.37±0.20°, 17.08±0.20°, 20.76±0.20°, 21.22±0.20°, 22.01±0.20° and 24.88±0.20°.

In some embodiments of the present disclosure, the X-ray powder diffraction pattern measured by Cu Kα radiation of the crystal form B of the acetate has characteristic diffraction peaks at the following 2θ angles: 6.18°, 10.57°, 11.94°, 12.37°, 12.94°, 13.93°, 16.22°, 17.08°, 17.93°, 18.30°, 19.47°, 20.34°, 20.76°, 21.22°, 21.58°, 22.01°, 22.25°, 23.06°, 24.07°, 24.46°, 24.88°, 25.28°, 25.69°, 25.99°, 26.66°, 27.03°, 28.85°, 29.54°, 31.14°, 31.88°, 32.48°, 33.70°, 34.43°, 35.54°, 36.33°, 37.89°, and 39.67°.

In some embodiments of the present disclosure, the X-ray powder diffraction pattern of the crystal form B of the acetate is shown in FIG. 4.

In some embodiments of the present disclosure, the peak positions and relative intensities of the diffraction peaks in the XRPD pattern measured by Cu Kα radiation of the crystal form B of the acetate are shown in the following Table 2:

TABLE 2

XRPD diffraction data of the crystal form B of the compound of formula (II-2)

| No. | 2θ (°) | d-Spacing (Å) | Intensity | Relative intensity (%) |
|---|---|---|---|---|
| 1 | 6.18 | 14.3 | 4109.68 | 100 |
| 2 | 10.57 | 8.37 | 721.3 | 17.55 |
| 3 | 11.94 | 7.41 | 2041.45 | 49.67 |
| 4 | 12.37 | 7.16 | 2590.18 | 63.03 |
| 5 | 12.94 | 6.84 | 758.47 | 18.46 |
| 6 | 13.93 | 6.36 | 946.38 | 23.03 |
| 7 | 16.22 | 5.47 | 834 | 20.29 |
| 8 | 17.08 | 5.19 | 2268.53 | 55.2 |
| 9 | 17.93 | 4.95 | 929.49 | 22.62 |
| 10 | 18.3 | 4.85 | 938.61 | 22.84 |
| 11 | 19.47 | 4.56 | 691.65 | 16.83 |
| 12 | 20.34 | 4.37 | 562.17 | 13.68 |
| 13 | 20.76 | 4.28 | 1986.28 | 48.33 |
| 14 | 21.22 | 4.19 | 2474.24 | 60.21 |
| 15 | 21.58 | 4.12 | 904.49 | 22.01 |
| 16 | 22.01 | 4.04 | 950.1 | 23.12 |
| 17 | 22.25 | 3.99 | 427.79 | 10.41 |
| 18 | 23.06 | 3.86 | 659.24 | 16.04 |
| 19 | 24.07 | 3.7 | 645.13 | 15.7 |
| 20 | 24.46 | 3.64 | 1005.52 | 24.47 |
| 21 | 24.88 | 3.58 | 2630.84 | 64.02 |
| 22 | 25.28 | 3.52 | 856.61 | 20.84 |
| 23 | 25.69 | 3.47 | 588.55 | 14.32 |
| 24 | 25.99 | 3.43 | 554.06 | 13.48 |
| 25 | 26.66 | 3.34 | 501.75 | 12.21 |
| 26 | 27.03 | 3.3 | 134.17 | 3.26 |
| 27 | 28.85 | 3.09 | 874.93 | 21.29 |
| 28 | 29.54 | 3.02 | 218.63 | 5.32 |
| 29 | 31.14 | 2.87 | 160.35 | 3.9 |
| 30 | 31.88 | 2.81 | 141.63 | 3.45 |
| 31 | 32.48 | 2.76 | 141.68 | 3.45 |
| 32 | 33.7 | 2.66 | 69.63 | 1.69 |
| 33 | 34.43 | 2.6 | 136.93 | 3.33 |
| 34 | 35.54 | 2.53 | 156.4 | 3.81 |
| 35 | 36.33 | 2.47 | 113.75 | 2.77 |
| 36 | 37.89 | 2.37 | 38.07 | 0.93 |
| 37 | 39.67 | 2.27 | 55.41 | 1.35 |

In some embodiments of the present disclosure, the differential scanning calorimetry (DSC) curve of the crystal form B of the acetate has an endothermic peak with an onset at 157.9° C.

In some embodiments of the present disclosure, the DSC pattern of the crystal form B of the acetate is shown in FIG. 5.

In some embodiments of the present disclosure, the thermogravimetric analysis (TGA) curve of the crystal form B of the acetate has a weight loss of 2.00% occurred at 120.0° C.±3° C.

In some embodiments of the present disclosure, the TGA pattern of the crystal form B of the acetate is shown in FIG. 6.

The present disclosure also provides a preparation method of the crystal form B of the acetate, and the method comprises the following steps:

1) dissolving a compound of formula (I) in an organic solvent, then adding acetic acid and stirring;
2) filtering under reduced pressure, collecting filter cake;
3) vacuum drying the filter cake.

In some embodiments of the present disclosure, the organic solvent is ethyl acetate in the preparation method of the crystal form B of the acetate.

The present disclosure also provides a use of the hydrochloride, the crystal form A of the hydrochloride, the acetate, and the crystal form B of the acetate in the manufacture of RHO inhibitor medicaments.

The present disclosure also provides a use of the hydrochloride, the crystal form A of the hydrochloride, the acetate, and the crystal form B of the acetate in the manufacture of a medicament for the treatment of pulmonary fibrosis and radiation pulmonary fibrosis.

Technical Effect

The preparation process of the crystal forms of the present disclosure is simple; the crystal forms are stable; the influence of heat and illumination in the crystal forms is small; and the crystal forms are convenient for preparation.

Definition and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The solvents used in the present disclosure are commercially available.

The present disclosure employs the following abbreviations:

ACN stands for acetonitrile; Bis-Tris stands for bis(2-hydroxyethyl)aminotris(hydroxymethyl)methane; DMSO stands for dimethyl sulfoxide.

The compounds of the present disclosure are named according to the conventional naming principles in the art or by ChemDraw® software, and the commercial compounds are named by the supplier directory.

The Instrument and Analysis Method of the Present Disclosure 1.1 X-Ray Powder Diffraction (X-Ray Powder Diffractometer, XRPD) Method Instrument model: X'pert3 X-ray diffractometer of PANalytical Company Detection method: about 10 mg of the sample was used for XRPD detection The detailed XRPD parameters were as follows:

Radioactive source: Cu, K$\alpha$1=1.540598 Å, Cu, K$\alpha$2=1.544426 Å

Tube voltage: 45 kV, tube current: 40 mA

Scanning angle range: 3-40 deg

Step time: 46.665 second 1.2. Differential Scanning Calorimetry (Differential Scanning Calorimeter, DSC)

Instrument model: TA 2500 differential scanning calorimeter

Test method: Samples (about 1-5 mg) were taken and placed in a DSC aluminum tray with a non-pierced cover and heated from 25° C. (room temperature) at a heating rate of 10° C./min under 50 mL/min $N_2$ until sample decomposition.

1.3 Thermogravimetric Analysis (Thermal Gravimetric Analyzer, TGA)

Instrument model: TA 5500 thermal gravimetric analyzer

Test method: Samples (about 1-5 mg) were taken and placed in an open TGA aluminum plate for testing, and the samples were heated from room temperature to 350° C. at a heating rate of 10° C./min under 10-25 mL/min $N_2$.

1.4 Elemental Chlorine Analysis Test 1.4.1 Instruments and Equipment

| Name | Model | Equipment number | Manufacturers | Valid until |
|---|---|---|---|---|
| Ion Chromatograph | LC-20ADSP | CAS-WH-IC-A | SHIMADZU | 9 Jul. 2021 |
| Analytical balance | XS205DU | CAS-WH-BAL-A | METTLER TOLEDO | 5 Sep. 2019 |
| Chromatographic columns | Shim-pack IC-A3 | CASWH-LC-15-0112 | SHIMADZU | N/A |
| Water Purifier | Milli-QIQ7000 | CAS-WH-PWG-E | Merck | 26 Dec. 2019 |

1.4.2 Instruments and Reagents

| Name | Grade/Purity | Batch number | Manufacturers | Valid until |
|---|---|---|---|---|
| Cl standard solution | 1000 μg/mL | 189003-1 | National Center for Analysis and Testing of Non-ferrous Metals and Electronic Materials | 4 Sep. 2020 |
| Water | 18.2 MΩ · cm | 20190717 | WuXi AppTec | 23 Jul. 2019 |

1.4.3 Solution Preparation

| | |
|---|---|
| Preparation of standard solution | Aspirating 1 mL of Cl⁻ standard solution in a 50 mL volumetric flask, diluting to scale with water and labeling as STD-Cl-1 Aspirating 1 mL of Cl⁻ standard solution in a 50 mL volumetric flask, diluting to scale with water and labeling as STD-Cl-2 |
| Preparation of sample solution | Weighing about 20 mg of sample in a 100 mL volumetric flask, dissolving and diluting with water to the scale and labeling as SPL1-1 Weighing about 20 mg of sample in a 100 mL volumetric flask, dissolving and diluting with water to the scale and labeling as SPL1-2 |

1.4.4 Method Information

| | |
|---|---|
| Method name | IC-A3 |
| Instrument | SHIMADZU LC-20AD sp |
| Software | Lab Solution Version 5.92 |
| Chromatographic columns | SHIMADZU Shim-pack IC-A3 4.6 mm*15 cm 5 μm |
| Mobile phase | 8.0 mmol/L p-Hydroxybenzoic acid + 3.2 mmol/L Bis(2-hydroxyethyl)aminotris(hydroxymethyl)methane (Bis-Tris) |
| Column temperature | 40° C. |
| Flow rate | 1.5 mL/min |
| Detectors | CDD-10A VP |
| LC stop time | 18 min |

1.5 Single Crystal X-Ray Diffraction Method

Instrument model: Bruker D8 Venture Photon II diffractometer

Light source: CuKα radiation

Scanning mode: φ/ω scanning

The total number of collected diffraction points was 16827, the number of independent diffraction points was 5091, and the number of observable points (I/sigma≥2) was 2177.

Test method: The direct method (Shelxs97) was used to analyze the crystal structure and obtain all 39 non-hydrogen atomic positions, then the least squares method was used to correct the structural parameters and discriminate the atomic species, and the geometric calculation method and the difference Fourier method were used to obtain all hydrogen atomic positions, and after refinement $R_1$=0.0783, $wR_2$=0.2735 (w=1/σ|F|$^2$), S=0.957.

DETAILED DESCRIPTION OF THE EMBODIMENT

Figure 1:
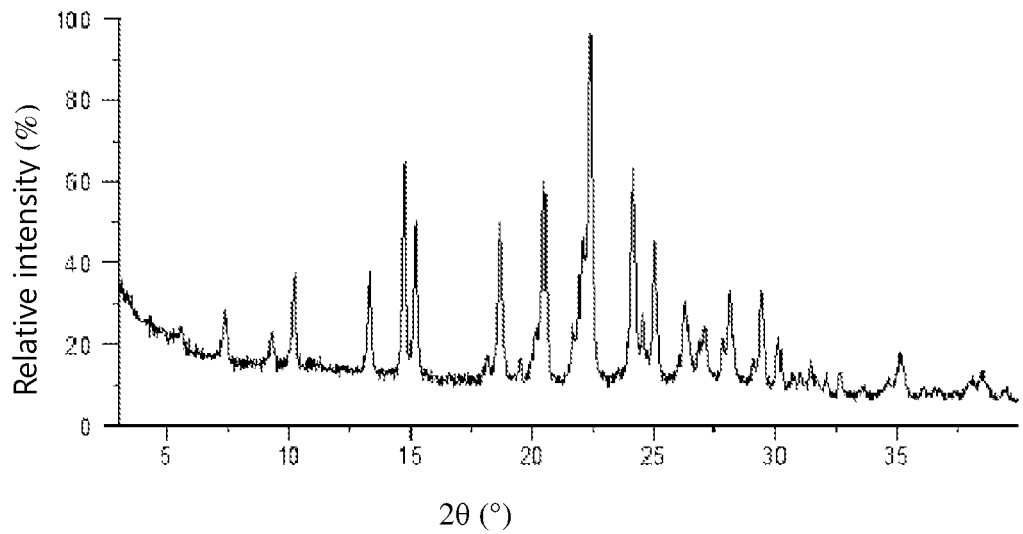
FIG. 1 is a XRPD pattern of the crystal form A of the compound of formula (II-1).
Figure 2:
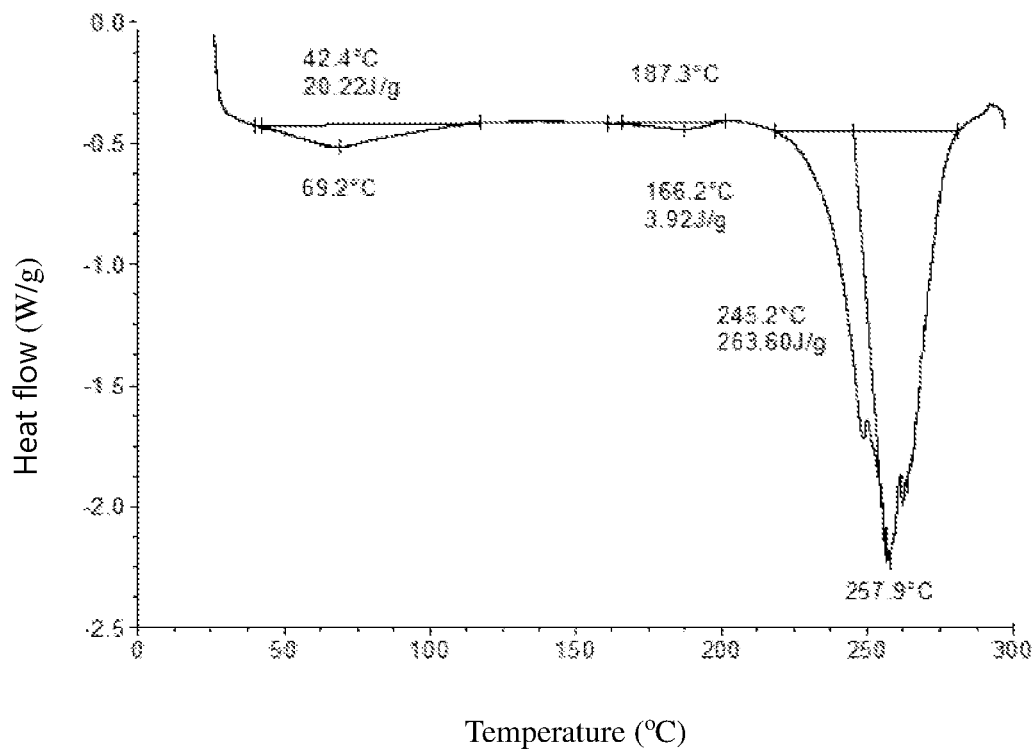
FIG. 2 is a DSC pattern of the crystal form A of the compound of formula (II-1).
Figure 3:
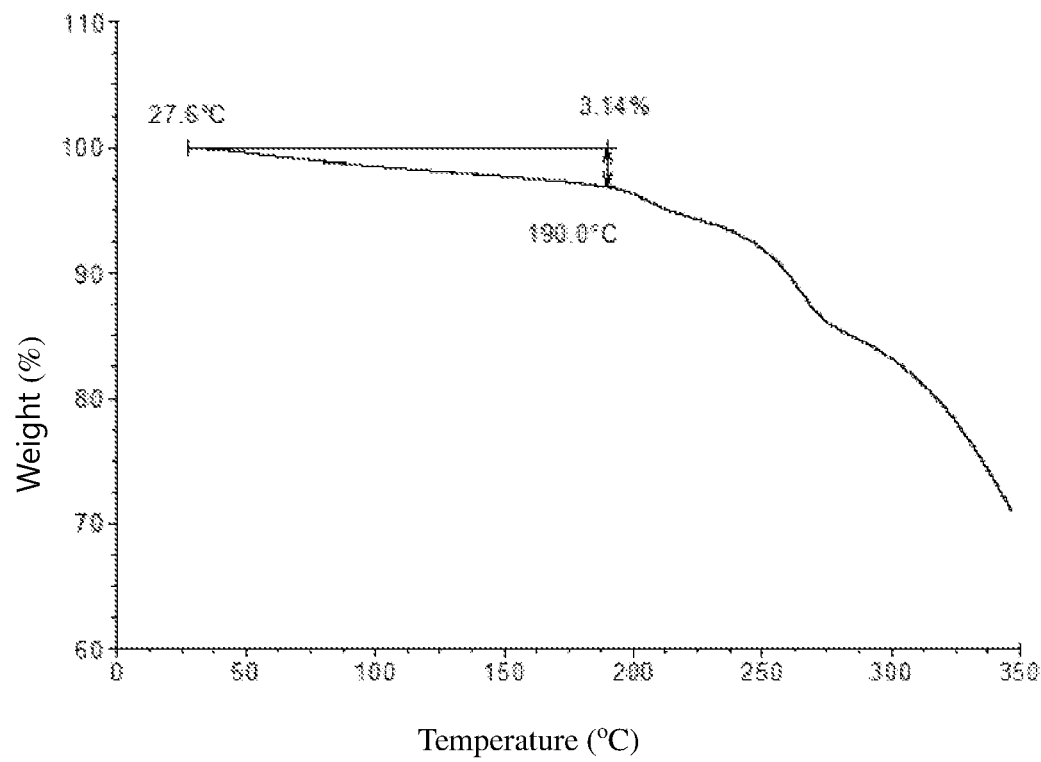
FIG. 3 is a TGA pattern of the crystal form A of the compound of formula (II-1).

The present disclosure will be specifically described below by way of embodiments, but the scope of the present disclosure is not limited thereto. The present disclosure has been described in detail herein, in which specific embodiments thereof are also disclosed, and various changes and modifications with respect to specific embodiments of the present disclosure will be apparent to those skilled in the art without departing from the spirit and scope of the present disclosure.

Preparation Embodiment

Embodiment 1: Preparation of Compound 2

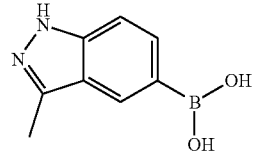

Synthetic Route:

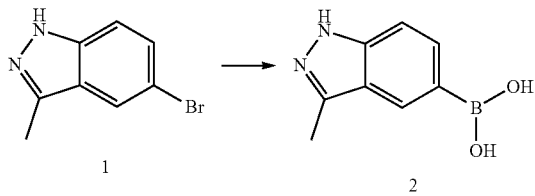

Ethanol (12.5 L) was added to a reaction kettle, then compound 1 (2.5 kg, 11.8 mol), tetrahydroxydiboron (1.06 kg, 11.8 mol) and potassium acetate (1.75 kg, 17.8 mol) were added successively, and the mixture was started to stir between 25 to 30° C. The reaction kettle was sealed, and the reaction system was replaced with nitrogen for three times. Then dichlorobis[di-tert-butyl-(4-dimethylaminophenyl)phosphine]palladium (41.3 g, 59.2 mmol) was added to the reaction kettle, and then the reaction kettle was sealed, and the reaction system was replaced with nitrogen for three times; the internal temperature was controlled at 50° C., and the mixture was stirred for 23 hours. After the reaction was completed, the distillation was continued under reduced pressure at an internal temperature of 50° C. (about 4 L of solvent was distilled out), and the heating was turned off. The concentrated reaction solution was diluted with 30 L of water and extracted with ethyl acetate (10 L×2, 5 L×1), and the combined organic phases were concentrated under reduced pressure. The obtained crude product was added to 2.8 M sodium hydroxide aqueous solution (10 L), and the mixture was stirred for 30 minutes, filtered; the filter cake was washed with water (1 L), and the obtained filtrate (15 L) was diluted with water (45 L); the pH of the solution was neutralized with 12 M hydrochloric acid to 6-7, and the mixture was stirred. At this time, solid would precipitate, and the mixture was filtered; the filter cake was added to water, stirred at 25° C. for 2.5 hours, filtered, and the filter cake was vacuum dried to obtain compound 2.

$^1$H NMR (400 MHz, DMSO-d6) δ 12.60 (s, 1H), 8.22 (s, 1H), 7.94 (s, 2H), 7.76 (dd, J=0.8 Hz, J=8.4 Hz, 1H), 7.40-7.38 (m, 1H), 2.51-2.52 (s, 3H). MS-ESI Calcd for [M+H]$^+$ 177, Found 177.

Embodiment 2: Preparation of the Compound of Formula (I-1)

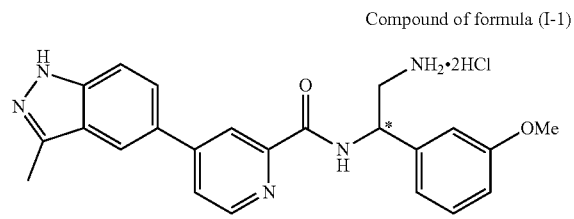

Compound of formula (I-1)

Synthetic Route:

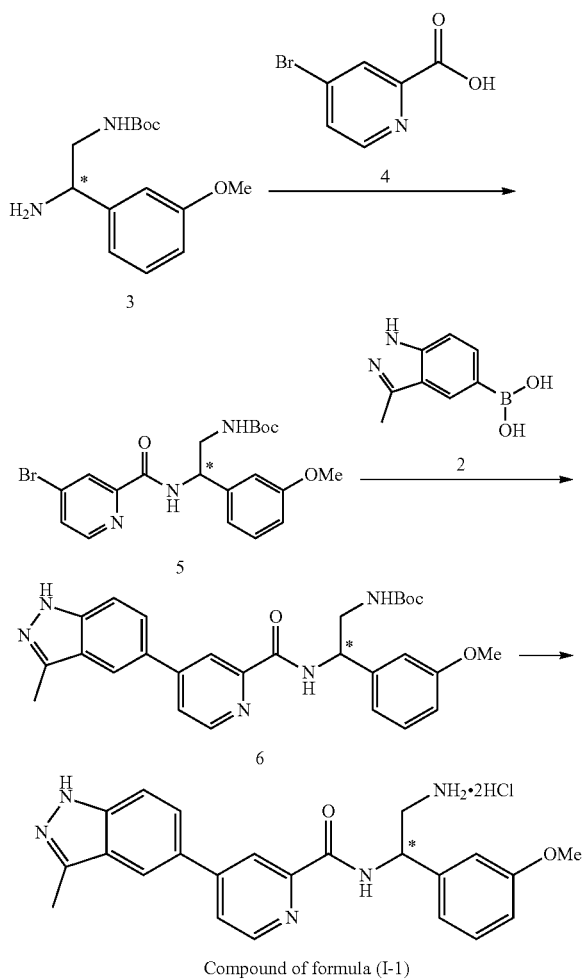

Step 1

N,N-Dimethylformamide (15 L) was added to a reaction kettle, and the stirring was turned on, and then compound 3 (1.50 kg, 5.63 mol, the carbon atom with "*" in compound 3 is a chiral carbon atom, which exists in a (R) or (S) single enantiomer form or a (R) or (S) single enantiomer-rich form) and compound 4 (1.19 kg, 5.91 mol) were added, and the internal temperature was controlled to 10 to 30° C., then N,N-diisopropylethylamine (1.96 L) was added; and a 50% ethyl acetate solution of tri-n-propylphosphonic anhydride (5.02 L) was slowly added in batches at an internal temperature of −5 to 5° C., and the reaction solution was stirred at 25° C. for 19 hours. After the reaction was completed, water (30 L) was added to the reaction solution, and a solid was precipitated; the mixture was stirred for 30 min, filtered under reduced pressure, and the filter cake was vacuum dried to obtain compound 5 (the carbon atom with "*" in compound 5 is a chiral carbon atom, which exists in a (R) or (S) single enantiomer form or a (R) or (S) single enantiomer-rich form).

$^1$H NMR (400 MHz, DMSO-d6) δ 9.19 (d, J=8.4 Hz, 1H), 8.57 (d, J=5.2 Hz, 1H), 8.14 (d, J=1.6 Hz, 1H), 7.86-7.96 (m, 1H), 7.26-7.22 (m, 1H), 7.03-7.06 (m, 1H), 6.88-6.98 (m, 2H), 6.78-6.87 (m, 1H), 5.03-5.19 (m, 1H), 3.74 (s, 3H), 3.39-3.51 (m, 1H), 3.24-3.34 (m, 1H), 1.32 (s, 9H).

MS-ESI Calcd for [M+H−t-Bu]$^+$393.396, Found 393.396.

Step 2

Dioxane (4.00 L) and water (1.00 L) were added to a reaction kettle, then compound 5 (1.00 kg, 2.22 mol), compound 2 (0.41 kg, 2.33 mol) and potassium phosphate (0.71 kg, 3.33 mol) were added successively with stirring, and the internal temperature was controlled to be less than 30° C. After the reaction system was replaced with nitrogen for three times, triphenylphosphine (28.8 g, 110 mmol) and tris(dibenzylideneacetone)dipalladium (50.3 g, 54.9 mmol) were added, then the reaction system was replaced with nitrogen for three times, and the mixture was stirred at 85° C. for 12 hours. After the reaction was completed, the temperature of the reaction solution was lowered to room temperature, and water (2.50 L) and ethyl acetate (2.50 L) were added to the reaction solution, and the mixture was stirred for 30 min. The mixture was filtered with diatomite, and the filter cake was rinsed with ethyl acetate (1.00 L×3). The filtrate was stood to separate the layers, and the aqueous phase was extracted with ethyl acetate (1.50 L×3); the organic phases were combined, washed with saturated brine (5.00 L), dried with anhydrous sodium sulfate (1.00 kg), and concentrated under reduced pressure to obtain a crude product. The crude product was added to tert-butyl methyl ether (10.0 L), and the mixture was stirred at 25° C. for 16 hours. The reaction solution was filtered under reduced pressure, and the filter cake was washed with tert-butyl methyl ether (1.00 L×3), collected, and concentrated under reduced pressure. The obtained crude product was dissolved in ethanol (10.0 L), and thiourea resin of equal mass to the crude product was added, and the mixture was stirred at 90° C. for 16 hours. The mixture was filtered while hot, and the filter cake was washed once with ethanol (1.00 L). The filtrate was put back into the reaction kettle, and thiourea resin of about equal mass to the crude product was added with stirring, and the mixture was stirred at 90° C. for 3 hours. The mixture was filtered while hot, and the filter cake was washed once with ethanol (1.00 L). The filtrate was put back into the reaction kettle, and thiourea resin of about half mass to the crude product was added with stirring, and the mixture was stirred at 90° C. for 3 hours. The reaction solution was then filtered while hot, and the filter cake was washed once with ethanol (1.00 L). The obtained filtrate was put back into the reaction kettle, and the system was replaced with nitrogen, then activated carbon about one-tenth of the mass of crude product was added, and the system was replaced with nitrogen again, and the mixture was stirred at 90° C. for 1 hour. The reaction solution was filtered while hot with diatomite under reduced pressure, and the filter cake was washed with ethanol (2.00 L×2), and the collected filtrate was concentrated under reduced pressure to obtain a crude product. tert-Butyl methyl ether (3.50 L) was added to the crude product and stirred at room temperature for 2 hours. The mixture was filtered under reduced pressure, and the filter cake was washed with tert-butyl methyl ether (500 mL×2), collected and vacuum dried to obtain compound 6 (the carbon atom with "*" in compound 6 is a chiral carbon atom, which exists in a (R) or (S) single enantiomer form or a (R) or (S) single enantiomer-rich form).

$^1$H NMR (400 MHz, DMSO-d6) δ 12.85 (s, 1H), 9.24-9.11 (m, 1H), 8.70 (d, J=5.2 Hz, 1H), 8.37-8.32 (m, 1H), 8.27 (s, 1H), 8.01-7.09 (m, 1H), 7.81-7.79 (m, 1H), 7.60 (d, J=8.4 Hz, 1H), 7.31-7.20 (m, 1H), 7.10-7.07 (m, 1H), 7.01-6.93 (m, 2H), 6.89-6.78 (m, 1H), 5.25-5.05 (m, 1H), 3.75 (s, 3H), 3.53-3.38 (m, 2H), 2.57 (s, 3H), 1.33 (s, 9H). MS-ESI Calcd for [M+H]$^+$ 502, Found 502.

Step 3

Compound 6 (451 g, 879 mmol) was dissolved in ethyl acetate (2.30 L). The stirring was started, then an ethyl acetate solution of hydrogen chloride (4 M, 2.30 L) was slowly added in batches, and the reaction was stirred at 25° C. for 16 hours. After the reaction was completed, the reaction solution was concentrated under reduced pressure, and the compound of formula (I-1) after concentration under reduced pressure was dissolved in water (1.30 L) and acetonitrile (900 mL); the mixture was stirred, dissolved and clarified, and then filtered under reduced pressure. The filtrate was transferred to a 30 L barrel, and acetonitrile (12 L) was added, and the mixture was stirred at 25° C. for 30 minutes. The mixture was filtered under reduced pressure, and the filter cake was washed with acetonitrile (500 mL×2). The filter cake was collected and vacuum dried (45° C., pressure<−0.1 MPa) to obtain a crude product of the compound of formula (I-1) (the carbon atom with "*" in the compound of formula (I-1) is a chiral carbon atom, which exists in a (R) or (S) single enantiomer form or a (R) or (S) single enantiomer-rich form).

MS-ESI Calcd for [M+H]$^+$402, Found 402.

Embodiment 3: Determination of Absolute Configuration of the Compound of Formula (I-1)

Synthesis of Compound Derivative 8 of Formula (I-1)

The compound of formula (I-1) (1.78 g, 4.43 mmol) and 4-bromobenzoic acid (compound 7, 0.98 g, 4.88 mmol) were weighed and dissolved in DMF (15 mL), and then diisopropylethylamine (2.31 mL, 13.3 mmol) and tri-n-propyl cyclic phosphonic anhydride (50% ethyl acetate solution) (3.95 mL, 6.64 mmol) were added. The reaction solution was stirred at 15° C. for 18 hours. The remaining compound of formula (I-1) was monitored by LCMS. Diisopropylethylamine (2.31 mL, 13.3 mmol) and tri-n-propyl cyclic phosphonic anhydride (50% ethyl acetate solution) (2.63 mL, 4.43 mmol) were added, and the reaction was continued to stir at 15° C. for 4 hours. The complete of the reaction was monitored by LCMS, and the reaction was stopped. Saturated sodium bicarbonate solution (20 mL) was added for quenching, and the mixture was extracted with ethyl acetate (20 mL×2). The organic phases were combined, washed with saturated sodium chloride solution (40 mL×2), dried with anhydrous sodium sulfate, filtered, and the filtrate was concentrated under reduced pressure. Compound 8 (the carbon atom with "*" in compound 8 is a chiral carbon atom, which exists in a (R) or (S) single enantiomer form or a (R) or (S) single enantiomer-rich form) was prepared and separated from the crude product by high performance liquid chromatography.

Single crystal culture process of compound 8: Compound 8 (10.66 mg, 18.2 μmol) was weighed, dissolved with 0.5 mL of methanol, filtered through an organic phase needle filter, and transferred to a 2 mL colorless clear glass flask. Needle-like crystals were obtained by standing and volatilizing at 15 to 25° C.

Figure 10:
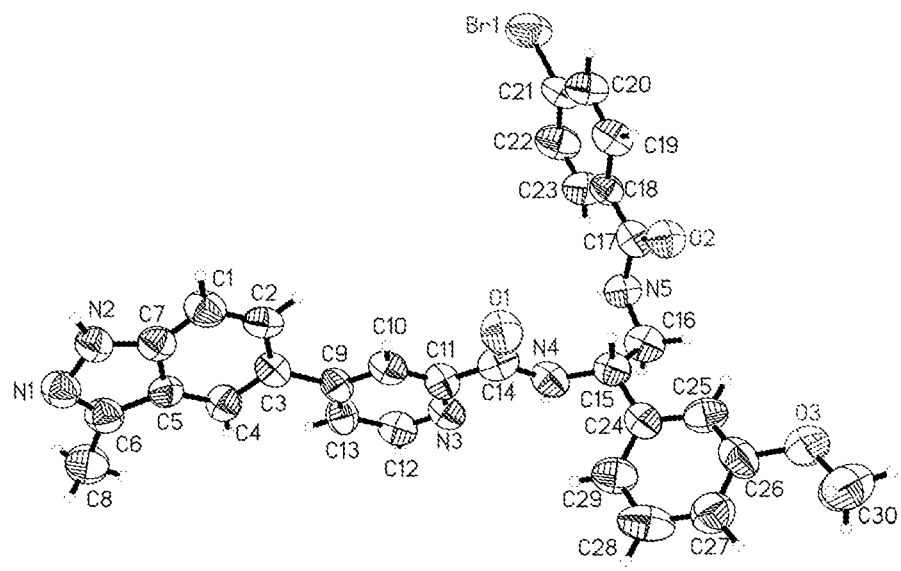
FIG. 10 is a single crystal X-ray diffraction pattern of compound 8.

From the single crystal diffraction results of compound 8, as shown in FIG. 10, it can be determined that it exists in a (S) single enantiomer form or a (S) single enantiomer-rich form, and its absolute configuration structure is as follows:

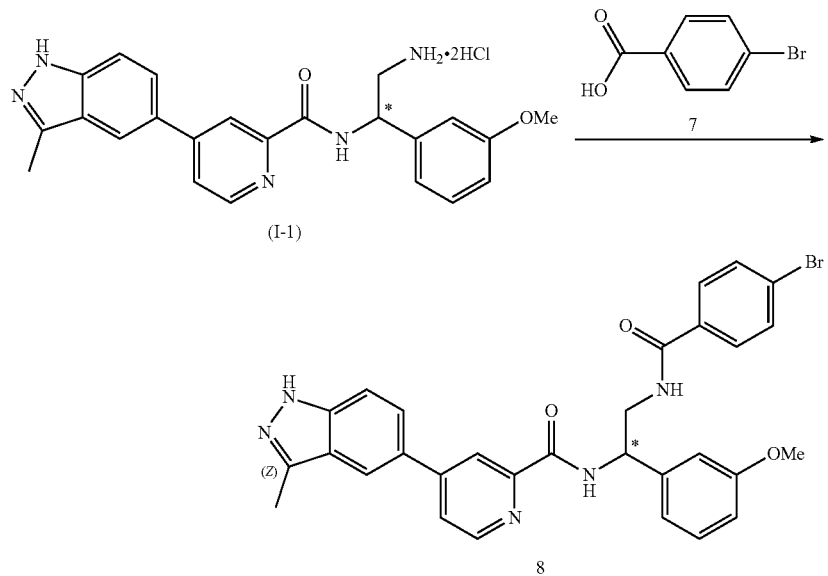

8

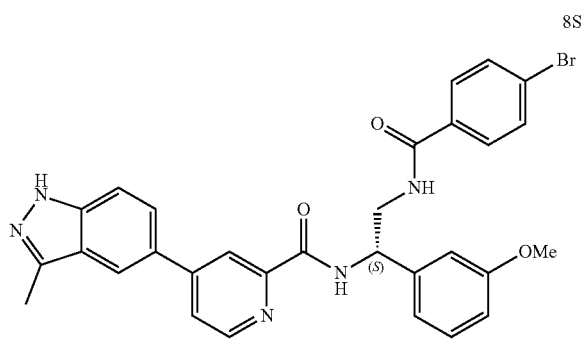

8S

The absolute configuration of the compound of formula (IA) can be determined from the absolute configuration of compound 8, having the structure shown in the following formula:

Compound of formula (II-1)

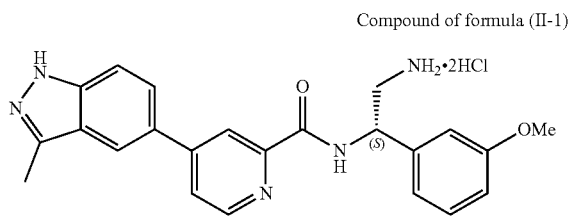

Embodiment 4: Preparation of the Crystal Form A of the Compound of Formula (II-1)

Compound of formula (II-1)

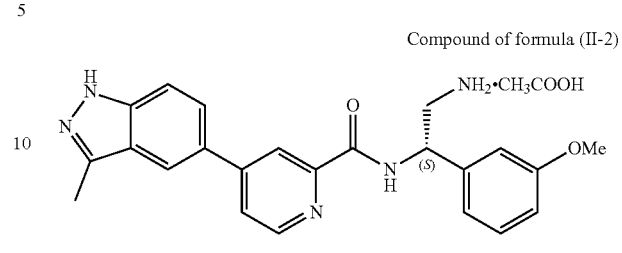

The dried compound of formula (II-1) (401 g, 0.85 mol) was put into a 5 L reaction flask, then ethanol (4 L) was added, and the mixture was stirred for 12 hours at 25° C. The mixture was filtered under reduced pressure; and the filter cake was washed with ethanol (200 mL×2), collected and vacuum dried (50° C., pressure<−0.1 Mp) to obtain the crystal form A of the compound of formula (II-1) by XRPD detection.

$^1$H NMR (400 MHz, DMSO-d6) δ 10.34-10.13 (m, 1H), 8.99 (s, 1H), 8.79 (d, J=5.6 Hz, 1H), 8.66 (s, 1H), 8.41 (s, 3H), 8.32-8.25 (m, 1H), 8.02 (dd, J=1.2, 8.8 Hz, 1H), 7.64 (d, J=8.8 Hz, 1H), 7.37-7.25 (m, 1H), 7.18 (s, 1H), 7.10 (d, J=8.0 Hz, 1H), 6.89 (dd, J=2.0, 8.0 Hz, 1H), 5.52-5.40 (m, 1H), 3.77 (s, 3H), 3.70-3.58 (m, 1H), 3.29-3.17 (m, 1H), 2.61 (s, 3H); MS-ESI Calcd for [M+H]$^+$ 402, Found 402; the chloride ion content test showed that the chloride ion content was 15.7%, and the compound of formula (II-1) contains two chlorine atoms.

Embodiment 5: Preparation of the Crystal Form B of the Compound of Formula (II-2)

Compound of formula (II-2)

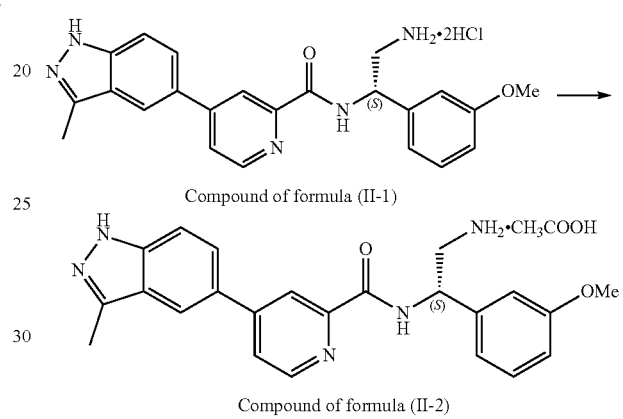

Synthetic Route:

Compound of formula (II-1)

Compound of formula (II-2)

Step 1

The compound of formula (II-1) (25.0 g, 52.7 mmol) after concentration under reduced pressure was diluted with water (100 mL), then the pH of the solution was adjusted to about 8 with saturated sodium bicarbonate aqueous solution, and the aqueous phase was poured out, and the compound was dissolved with ethanol (100 mL) and concentrated under reduced pressure. The aqueous phase was then extracted with ethyl acetate (200 mL×3), and the combined organic phases were washed with saturated brine (150 mL×1), dried with anhydrous sodium sulfate, filtered, and all the above organic phases were concentrated under reduced pressure. The obtained crude product was purified by high performance liquid chromatographic column (alkaline) to obtain the compound of formula (I), MS-ESI Calcd for [M+H]$^+$ 402, Found 402. The absolute configuration of the compound of formula (I-1) can be determined from the absolute configuration of the compound of formula (II-1), having the structure shown in the following formula (II):

Compound of formula (II)

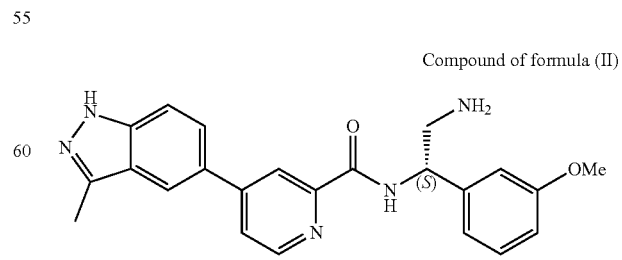

The compound of formula (II) (1.05 g, 2.62 mmol) was dissolved in ethyl acetate (30 mL), then acetic acid (310 μL)

was added at room temperature, and the mixture was stirred for 24.5 hours. The mixture was filtered under reduced pressure, and the filter cake was dried to dryness under reduced pressure at 45° C. with an oil pump. The crystal form B of the compound of formula (II-2) was obtained by XRPD detection.

$^1$H NMR (400 MHz, DMSO-d6) δ 9.21 (d, J=8.4 Hz, 1H), 8.80-8.64 (m, 1H), 8.34 (d, J=1.6 Hz, 1H), 8.26 (s, 1H), 8.01-7.997 (m, 1H), 7.80 (dd, J=1.6, 8.8 Hz, 1H), 7.60 (d, J=8.4 Hz, 1H), 7.26-7.22 (m, 1H), 7.01-6.92 (m, 2H), 6.86-6.76 (m, 1H), 5.10-4.93 (m, 1H), 3.73 (s, 3H), 3.08-3.03 (m, 1H), 2.99-2.90 (m, 1H), 2.56 (m, 3H), 1.88 (s, 3H). MS-ESI Calcd for [M+H]$^+$ 402, Found 402.

Characterization Embodiment

Embodiment 1: Solid Stability Test of the Crystal Form A of the Compound of Formula (II-1)

According to the "Guidelines for the Stability Test of APIs and Preparations" (Chinese Pharmacopoeia 2015 Edition Part IV general rules 9001), the stability of the crystal form A of the compound of formula (II-1) was investigated at high temperature (60° C., open), high humidity (room temperature/relative humidity (RH) 92.5%, open) and strong illumination (total illumination=1.2×10$^6$ Lux•hr/near UV=200 w•hr/m$^2$, open).

About 10 mg of the crystal form was accurately weighed and added to a dry and clean glass flask, spread into a thin layer, covered with aluminum foil, pierced small holes and placed under the influence factor test conditions and under accelerated conditions. Samples placed under illumination (visible light 1200000 Lux, UV 200 W) conditions were placed in clear glass flasks, fully exposed, and samples used for XRPD detection were placed separately.

After the samples were removed at the time point, the cover was covered, and the flask was sealed using sealing film, and stored in −20° C. refrigerator. When preparing the sample, the sample was removed from the refrigerator, restored to room temperature; 10 mL of 80% ACN was added, and the sample was dissolved by sonication for 2 min to obtain a solution with a concentration of about 1 mg/mL, then the liquid phase was used for injection analysis, and the detection results were compared with the initial detection results on day 0. The test results are shown in the following Table 3.

Preparation of standard solution on day 0: About 10 mg of the crystal was weighed and added to a 10 mL volumetric flask, dissolved with 80% ACN and the volume was fixed to the scale.

TABLE 3

Solid stability test results of the crystal form A of the compound of formula (II-1)

| Test condition | Time point | Crystal form |
|---|---|---|
| — | 0 day | Crystal form A |
| High temperature (60° C., open) | 5 days | Crystal form A |
|  | 10 days | Crystal form A |
| High humidity (relative humidity 75%, open) | 5 days | Crystal form A |
|  | 10 days | Crystal form A |
| High humidity (relative humidity 92.5%, open) | 5 days | Crystal form C |
|  | 10 days | Crystal form C |
| High temperature and humidity (40° C. relative humidity 75%, open) | 5 days | Crystal form A |
|  | 10 days | Crystal form A |
| High temperature and humidity (60° C. relative humidity 75%, open) | 5 days | Crystal form A |
|  | 10 days | Crystal form A |

TABLE 3-continued

Solid stability test results of the crystal form A of the compound of formula (II-1)

| Test condition | Time point | Crystal form |
|---|---|---|
| Illumination (total illuminance = 1.2 × 10$^6$ Lux · hr/near UV = 200 w · hr/m$^2$, open) | 5 days | Crystal form A |
|  | 10 days | Crystal form A |

Figure 7:
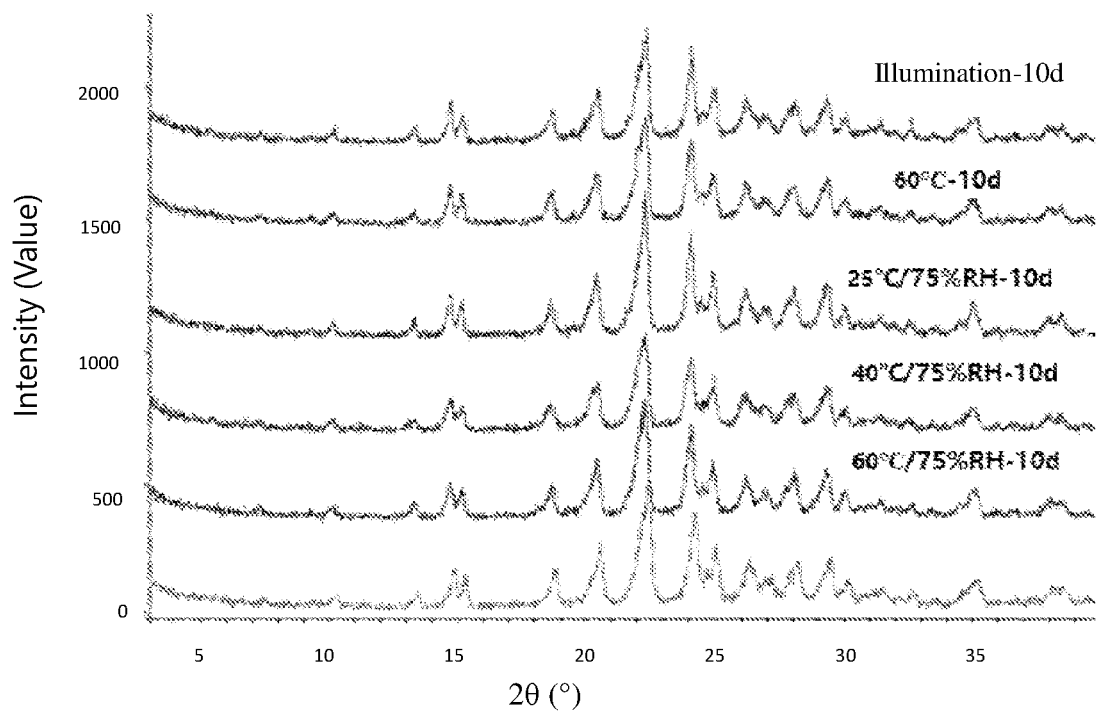
FIG. 7 is a comparison XRPD pattern of the crystal form A of the compound of formula (II-1) under high temperature, high humidity and illumination conditions.
Figure 8:
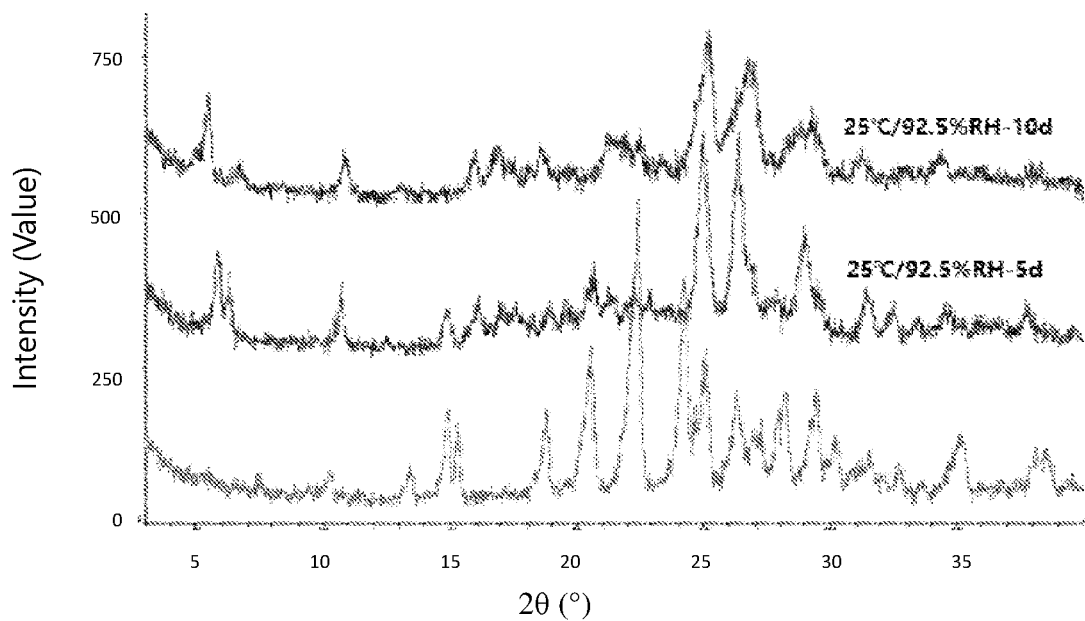
FIG. 8 is a comparison XRPD pattern of the crystal form A of the compound of formula (II-1) under 92.5% high humidity.

Conclusion: The crystal form A of the compound of formula (II-1) has good stability at high temperature, 75% humidity and strong illumination conditions as shown in FIG. 7, but under 92.5% high humidity conditions, crystal transformation will occur as shown in FIG. 8.

Embodiment 2: Influence Factors and Accelerated Stability Test of the Crystal Form A of the Compound of Formula (II-1)

Stability studies of the crystal form A of the compound of formula (II-1) in influence factor test:

High humidity (25° C./92.5% RH): 1 g of each sample was weighed and the sample was placed in an open flat weighing bottle (70×35 mm) under 25° C./92.5% RH conditions, and then placed in a comprehensive drug stability chamber (25° C./92.5% RH) for investigation.

High temperature (60° C.): 1 g of each sample was weighed and the sample was placed in an open flat weighing bottle under 60° C. conditions, and then placed in a blast drying oven (60° C.) for investigation.

Illumination: 1 g of each sample was weighed. The samples with illumination condition were placed in a clean watch glass, spread into a thin layer and put into 5000±500 lux (visible light) with 90 μw/cm$^2$ (UV) conditions for illumination.

The experimental results are shown in the following Table 4:

TABLE 4

Stability test results of influence factors of the crystal form A of the compound of formula (II-1)

| Research conditions Time | / 0 day | 60° C. 1 month | 25° C./92.5% RH 1 month | Illumination 10 days |
|---|---|---|---|---|
| Relative retention time (RRT) 0.66 | 0.06% | 0.06% | 0.06% | 0.09% |
| 0.85 | 0.34% | 0.31% | 0.32% | 0.31% |
| 0.90 | 0.02% | 0.06% | 0.03% | 0.02% |
| 1.64 | 0.06% | 0.04% | 0.05% | 0.05% |
| Total impurities | 0.46% | 0.43% | 0.43% | 0.51% |
| Content | 99.5% | 99.6% | 98.9% | 97.6% |

The results show that the crystal form A of the compound of formula (II-1) is stable under the conditions of illumination, high temperature and high humidity, and the main impurities and total impurities have no obvious change.

Stability studies of the crystal form A of the compound of formula (II-1) in accelerated test:

Accelerated stability test: each sample was weighed 0.8 g (accelerated 1 month, accelerated 2 months) or 1.2 g (accelerated 3 months, accelerated 6 months) into double-layer low-density polyethylene (LDPE) bags, and each layer of LDPE bags was pierced and sealed, and then the LDPE bags were put into aluminum foil bags and heat sealed, respectively, and put into 40° C./75% RH conditions for investigation. The experimental results are shown in the following Table 5:

TABLE 5

Accelerated stability test results of the crystal
form A of the compound of formula (II-1)

| Research conditions | | 40° C./75% RH | | | |
|---|---|---|---|---|---|
| Time | | 0 day | 1 month | 2 months | 3 months |
| RRT | 0.66 | 0.06% | 0.06% | 0.06% | 0.06% |
| | 0.85 | 0.34% | 0.36% | 0.33% | 0.33% |
| | 0.90 | 0.02% | 0.02% | 0.03% | 0.04% |
| | 1.64 | 0.06% | 0.05% | 0.04% | 0.04% |
| Total impurities | | 0.46% | 0.47% | 0.39% | 0.39% |
| Content | | 99.5% | 100.0% | 99.6% | 98.8% |

The results show that the crystal form A of the compound of formula (II-1) is stable under long-term placement conditions.

Embodiment 3: Solid Stability Test of the Crystal Form B of the Compound of Formula (II-2)

According to the "Guidelines for the Stability Test of APIs and Preparations" (Chinese Pharmacopoeia 2015 Edition Part IV general rules 9001), the stability of the crystal form B of the compound of formula (II-2) was investigated at high temperature (60° C., open), high humidity (room temperature/relative humidity (RH) 92.5%, open) and strong illumination (total illumination=$1.2 \times 10^6$ Lux•hr/near UV=200 w•hr/m$^2$, open).

About 10 mg of the crystal form was accurately weighed and added to a dry and clean glass flask, spread into a thin layer, covered with aluminum foil, pierced small holes and placed under the influence factor test conditions and under accelerated conditions. Samples placed under illumination (visible light 1200000 Lux, UV 200 W) conditions were placed in clear glass flasks, fully exposed, and samples used for XRPD detection were placed separately.

After the samples were removed at the time point, the cover was covered, and the flask was sealed using sealing film, and stored in −20° C. refrigerator. When preparing the sample, the sample was removed from the refrigerator, restored to room temperature; 80% ACN (10 mL) was added, and the sample was dissolved by sonication for 2 min to obtain a solution with a concentration of about 1 mg/mL, then the liquid phase was used for injection analysis, and the detection results were compared with the initial detection results on day 0. The test results are shown in the following Table 6.

Preparation of standard solution on day 0: About 10 mg of the crystal form was weighed and added to a 10 mL volumetric flask, dissolved with 80% ACN and the volume was fixed to the scale.

TABLE 6

Solid stability test results of the crystal form B of the
compound of formula (II-2)

| Test condition | Time point | Crystal form |
|---|---|---|
| — | 0 day | Crystal form B |
| High temperature (60° C., open) | 5 days | Crystal form B |
| | 10 days | Crystal form B |
| High humidity (relative humidity 75%, open) | 5 days | Crystal form B |
| | 10 days | Crystal form B |
| High humidity (relative humidity 92.5%, open) | 5 days | Crystal form B |
| | 10 days | Crystal form B |
| High temperature and humidity (40° C. relative humidity 75%, open) | 5 days | Crystal form B |
| | 10 days | Crystal form B |
| High temperature and humidity (40° C. relative humidity 75%, open) | 5 days | Crystal form B |
| | 10 days | Crystal form B |
| Illumination (total illuminance = $1.2 \times 10^6$ Lux · hr/ near UV = 200 w · hr/m$^2$, open) | 5 days | Crystal form B |
| | 10 days | Crystal form B |

Figure 9:
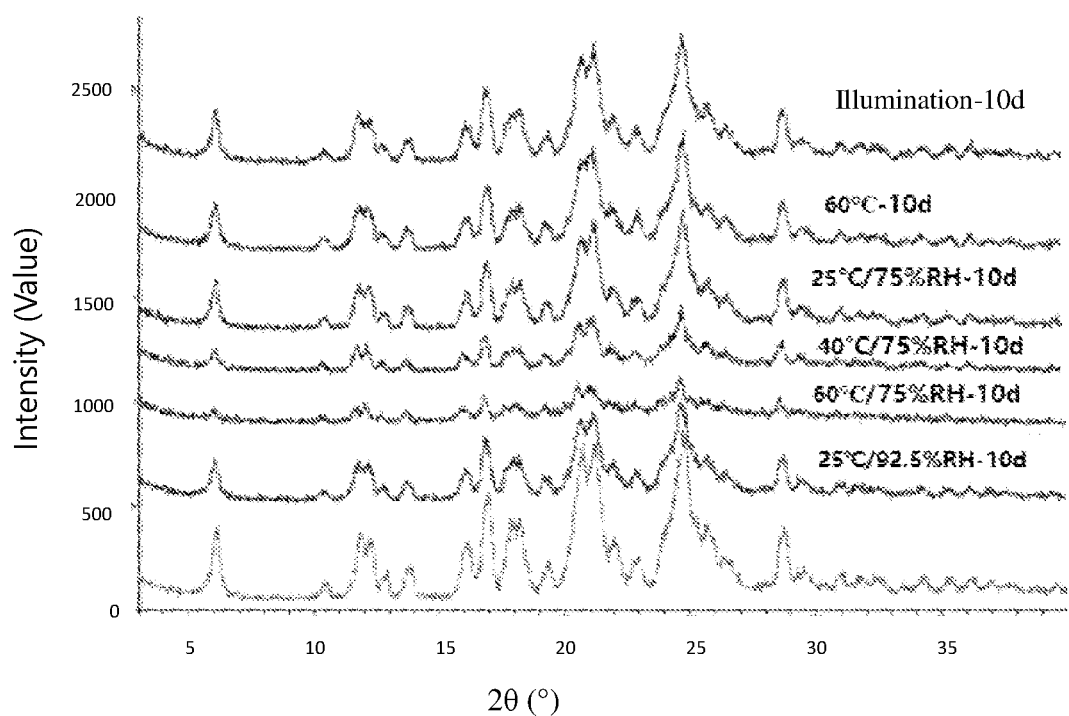
FIG. 9 is a comparison XRPD pattern of the crystal form B of the compound of formula (II-2) under high temperature, high humidity and illumination conditions.

Conclusion: The crystal form B of the compound of formula (II-2) has good stability at high temperature, high humidity and strong illumination conditions as shown in FIG. 9.

Activity Test

1. In Vitro Evaluation of ROCK Protein Kinase Inhibitory Activity

Experimental purpose: To detect the $IC_{50}$ value of ROCK protein kinase inhibition of compounds.

Experimental materials: assay buffer solution: 20 mM 4-hydroxyethyl piperazine ethanesulfonic acid (pH 7.5), 10 mM magnesium chloride, 1 mM ethylene glycol diethyl ether diaminetetraacetic acid, 0.02% polyoxyethylene lauryl ether, 0.02 mg/mL bovine serum albumin, 0.1 mM sodium vanadate, 2 mM dithiothreitol, 1% DMSO.

Experimental operation: ROCK protein kinase substrate Long S6 Kinase substrate peptide was added to a freshly prepared buffer solution at a concentration of 20 μM, then 1 nM ROCK protein kinase was added, and the mixture was stirred evenly. A series of DMSO diluents containing the compounds to be tested were added with Echo550 (started at 10M, diluted by 3 times series), preincubated at room temperature for 20 minutes, and $^{33}$P-ATP (radiation intensity 10 μCi/μL) was added to initiate the reaction, and the reaction was carried out for 2 hours at room temperature. The mixture was then filtered using P81 ion exchange paper (Whatman #3698-915) and washed with 0.75% phosphoric acid. Radiation intensity was detected using the Filter-Binding method.

The protein kinase inhibitory activity of the compound was expressed as the residual protein kinase activity relative to the blank substrate (DMSO alone). $IC_{50}$ values and curves were calculated using the Prism software package (Graph-Pad Software, San Diego Calif., USA).

Experimental Results:

TABLE 7

Test results of ROCK inhibitory activity
of the compound of formula (I)

| Compound | $IC_{50}$ for ROCK1 (nM) | $IC_{50}$ for ROCK2 (nM) |
|---|---|---|
| Compound of formula (II) | 13 | 2 |

Conclusion: The compound of formula (II) has good inhibitory activity against ROCK2, and also has some selectivity for ROCK2.

2. Pharmacokinetic Evaluation 2.1 Pharmacokinetic Study of the Racemate of the Compound of Formula (I) in SD Rats Experimental purpose: To study the pharmacokinetics of the compounds in SD rats Experimental material: SD rats (male, 7-10 weeks old, WTLH/SLAC)

Experimental procedure: The pharmacokinetic characteristics of the compounds were tested in rodents after intravenous (IV) and oral (PO) administration using standard protocols. The candidate compounds were prepared into 0.2 mg/mL clarified solutions and administrated to rats for single intravenous injection and oral administration. The solvent for both intravenous and oral administration was 5% DMSO/95% (10% hydroxypropyl β-cyclodextrin) aqueous solution. Four male SD rats were used in this project, and two rats were administered intravenously at a dose of 1 mg/kg and plasma samples were collected at 0.0833, 0.25, 0.5, 1, 2, 4, 6, 8 and 24 h after administration, and the other two rats were administered orally by gavage at a dose of 2 mg/kg and plasma samples were collected at 0.25, 0.5, 1, 2, 3, 4, 6, 8 and 24 h after administration. Whole blood samples were collected within 24 hours, centrifuged at 3000 g for 15 minutes, and the supernatant was separated to obtain plasma samples, and the proteins were precipitated by adding acetonitrile solution containing internal standard; the mixture was well mixed and centrifuged, and the supernatant was injected for quantitative analysis of plasma drug concentrations by LC-MS/MS analysis method, and pharmacokinetic parameters were calculated, such as peak concentration ($C_{max}$), clearance rate (CL), half-life ($T_{1/2}$), tissue distribution (Vdss), area under the drug-time curve ($AUC_{0-last}$), bioavailability (F), etc.

The pharmacokinetic related parameters of the embodiments of the present disclosure in rats are shown in the following Table 8.

Conclusion: The racemate of the compound of formula (I) has good pharmacokinetic properties, including good oral bioavailability, oral exposure, half-life and clearance rate, etc.

2.2 Pharmacokinetic Study of the Crystal Form a of the Compound of Formula (II-1) in SD Rats Experimental Purpose: To Study the Pharmacokinetics of the Compounds in SD Rats Experimental Materials: SD Rats (12, Half Male and Half Female)

Experimental procedure: The pharmacokinetic characteristics of the compounds were tested in rodents after intravenous (IV) and oral (PO) administration using standard protocols. The candidate compounds were prepared into 0.5 mg/mL and 1 mg/mL clarified solutions and administrated to rats for single intravenous injection and oral administration. The solvent for both intravenous and oral administration was 5% DMSO/95% (10% hydroxypropyl β-cyclodextrin) aqueous solution. 12 SD rats were used in this project, and 6 rats (half male and half female) were administered intravenously at a dose of 1 mg/kg and plasma samples were collected at 0.0833, 0.25, 0.5, 1, 2, 4, 8, 12, and 24 h after administration, and the other 6 rats (half male and half female) were administered orally by gavage at a dose of 10 mg/kg and plasma samples were collected at 0.25, 0.5, 1, 2, 4, 8, 12 and 24 h after administration. 15 µL of plasma sample was added to a 96-well plate, and 300 µL of internal standard working solution (MeOH (containing 1.00 ng/mL Verapamil and 0.1% formic acid (FA)): ACN (v:v, 50:50) solution) was added to precipitate the proteins, the 96-well plate was shaken for 15 min, followed by centrifugation at 4° C., 3220 g for 15 min. 150 µL of supernatant was placed in a new 96-well plate with 150 µL of aqueous solution containing 0.1% formic acid (FA) and shaken for 10 min, and then centrifuged at 4° C., 3220 g for 5 min. The samples were directly injected, and the plasma drug concentration was quantitatively analyzed by LC-MS/MS analysis method, and pharmacokinetic parameters were calculated, such as peak concentration ($C_{max}$), clearance rate (CL), half-life ($T_{1/2}$), tissue distribution (Vdss), area under the drug-time curve ($AUC_{0-last}$), bioavailability (F), etc.

The pharmacokinetic related parameters of the crystal form A of the compound of formula (II-1) of the present disclosure in rats are shown in the following Table 9.

TABLE 8

| | Pharmacokinetic test results | | | | | |
|---|---|---|---|---|---|---|
| Compound | Peak concentration $C_{max}$ (nM) | Clearance rate CL (mL/min/kg) | Tissue distribution Vdss (L/kg) | Half-life $T_{1/2}$ (IV, h) | Area under drug-time curve $AUC_{0-last}$ PO (nM · hr) | Bioavailability F (%) |
| Racemate of compound of formula (I) | 117 | 23.4 | 6 | 3.58 | 758 | 21 |

TABLE 9

Pharmacokinetic test results of the crystal form A of the compound of formula (II-1)

| Compound | Peak concentration $C_{max}$ (nM) | Clearance rate CL (mL/min/kg) | Tissue distribution Vdss (L/kg) | Half-life $T_{1/2}$ (IV, h) | Area under drug-time curve $AUC_{0-last}$ PO (nM · hr) | Bioavailability F (%) |
|---|---|---|---|---|---|---|
| Crystal form A of compound of formula (II-1) | 519 | 22.4 | 7.39 | 4.93 | 3690 | 17.8 |

Conclusion: The crystal form A of the compound of formula (II-1) has good pharmacokinetic properties in rats, including good oral bioavailability, oral exposure, half-life and clearance rate, etc.

2.3 Pharmacokinetic Study of the Crystal Form a of the Compound of Formula (II-1) in Beagle Dogs Experimental purpose: To study the pharmacokinetics of the compounds in Beagle dogs Experimental materials: Beagle dogs (12, half male and half female)

Experimental procedure: The pharmacokinetic characteristics of the compounds were tested in Beagle dogs after intravenous (IV) and oral (PO) administration using standard protocols. The candidate compounds were prepared into 0.5 mg/mL and 1.5 mg/mL clarified solutions and administrated to Beagle dogs for single intravenous injection and oral administration. The solvent for both intravenous and oral administration was 5% DMSO/95% (10% hydroxypropyl β-cyclodextrin) aqueous solution. 12 beagle dogs were used in this project, 6 beagle dogs (half male and half female) were administered intravenously at a dose of 1 mg/kg and plasma samples were collected at 0.083, 0.25, 0.25, 0.5, 1, 2, 4, 8, 12, 24, 36, 48 and 72 h after administration, and the other 6 beagle dogs (half male and half female) were administered orally by gavage at a dose of 7.5 mg/kg and plasma samples were collected at 0.25, 0.5, 1, 2, 4, 8, 12, 24, 36, 48 and 72 h after administration. 15 µL of plasma sample was added to a 96-well plate, and 300 µL of internal standard working solution (MeOH (containing 1.00 ng/mL Verapamil and 0.1% formic acid (FA)): ACN (v:v, 50:50) solution) was added to precipitate the proteins, the 96-well plate was shaken for 15 min, followed by centrifugation at 4° C., 3220 g for 15 min. 150 µL of supernatant was placed in a new 96-well plate with 150 µL of aqueous solution containing 0.1% formic acid (FA) and shaken for 10 min, and then centrifuged at 4° C., 3220 g for 5 min. The sample was directly injected, and the plasma drug concentration was quantitatively analyzed by LC-MS/MS analysis method, and pharmacokinetic parameters were calculated, such as peak concentration ($C_{max}$), clearance rate (CL), half-life ($T_{1/2}$), tissue distribution (Vdss), area under the drug-time curve ($AUC_{0-last}$), bioavailability (F), etc.

The pharmacokinetic related parameters of the crystal form A of the compound of formula (II-1) of the present disclosure in beagle dogs are shown in the following Table 10.

TABLE 10

Pharmacokinetic test results of the crystal form A of the compound of formula (II-1)

| Compound | Peak concentration $C_{max}$ (nM) | Clearance rate CL (mL/min/kg) | Tissue distribution Vdss (L/kg) | Half-life $T_{1/2}$ (IV, h) | Area under drug-time curve $AUC_{0-last}$ PO (nM · hr) | Bioavailability F (%) |
|---|---|---|---|---|---|---|
| Crystal Form A of compound of formula (II-1) | 834 | 22.3 | 18.6 | 12.4 | 12600 | 90.4 |

Conclusion: The crystal form A of the compound of formula (II-1) has good pharmacokinetic properties in beagle dogs, including good oral bioavailability, oral exposure, half-life and clearance rate, etc.

What is claimed is:

1. A crystal form A of the hydrochloride having a structure shown in formula (II-1), wherein, the X-ray powder diffraction pattern thereof measured by Cu Kα radiation has characteristic diffraction peaks at the following 2θ angles: 14.77±0.20°, 20.50±0.20°, 22.38±0.20° and 24.15±0.20°;

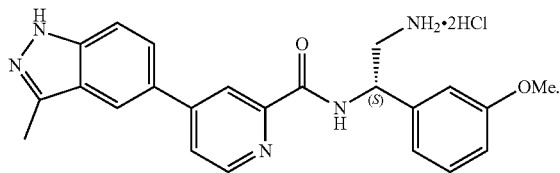

(I-1)

2. The crystal form A as defined in claim 1, wherein, the X-ray powder diffraction pattern thereof measured by Cu Kα radiation has characteristic diffraction peaks at the following 2θ angles: 10.22±0.20°, 13.36±0.20°, 14.77±0.20°, 18.69±0.20°, 20.50±0.20°, 22.38±0.20°, 24.15±0.20° and 25.03±0.20°.

3. The crystal form A as defined in claim 2, wherein, the X-ray powder diffraction pattern thereof measured by Cu Kα radiation has characteristic diffraction peaks at the following 2θ angles: 7.38°, 9.32°, 10.22°, 13.36°, 14.77°, 15.21°, 18.69°, 20.50°, 21.69°, 22.08°, 22.38°, 24.15°, 24.58°, 25.03°, 26.28°, 27.13°, 28.15°, 29.44°, 30.15°, 31.49°, 32.1°, 32.69°, 35.17° and 38.51°.

4. The crystal form A as defined in claim 2, wherein, the XRPD pattern thereof is shown in FIG. 1.

5. The crystal form A as defined in claim 4, wherein, the differential scanning calorimetry curve thereof has an endothermic peak with an onset at 245.2° C.±3° C.

6. A preparation method of the crystal form A as defined claim 1, comprising the following steps:
  1) adding a compound of formula (I-1) to an organic solvent and stirring at an appropriate temperature;
  2) filtering under reduced pressure, collecting filter cake;
  3) vacuum drying the filter cake.

7. The preparation method as defined in claim 6, wherein, the organic solvent is ethanol;
  or, the appropriate temperature is 25° C.;
  or, the stirring time is 10-12 hours.

8. A crystal form B of the acetate having a structure shown in formula (II-2), wherein, the X-ray powder diffraction pattern thereof measured by Cu Kα radiation has characteristic diffraction peaks at the following 2θ angles: 6.18±0.20°, 12.37±0.20°, 17.08±0.20°, 21.22±0.20° and 24.88±0.20°;

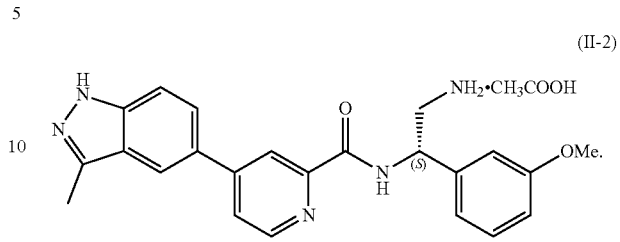

(II-2)

9. The crystal form B as defined in claim 8, wherein, the X-ray powder diffraction pattern thereof measured by Cu Kα radiation has characteristic diffraction peaks at the following 2θ angles: 6.18±0.20°, 11.94±0.20°, 12.37±0.20°, 17.08±0.20°, 20.76±0.20°, 21.22±0.20°, 22.01±0.20° and 24.88±0.20°.

10. The crystal form B as defined in claim 9, wherein, the X-ray powder diffraction pattern thereof measured by Cu Kα radiation has characteristic diffraction peaks at the following 2θ angles: 6.18°, 10.57°, 11.94°, 12.37°, 12.94°, 13.93°, 16.22°, 17.08°, 17.93°, 18.30°, 19.47° 20.34°, 20.76°, 21.22°, 21.58°, 22.01°, 22.25°, 23.06°, 24.07°, 24.46°, 24.88°, 25.28°, 25.69°, 25.99°, 26.66°, 27.03°, 28.85°, 29.54°, 31.14°, 31.88°, 32.48°, 33.70°, 34.43°, 35.54°, 36.33°, 37.89°, and 39.67°.

Figure 4:
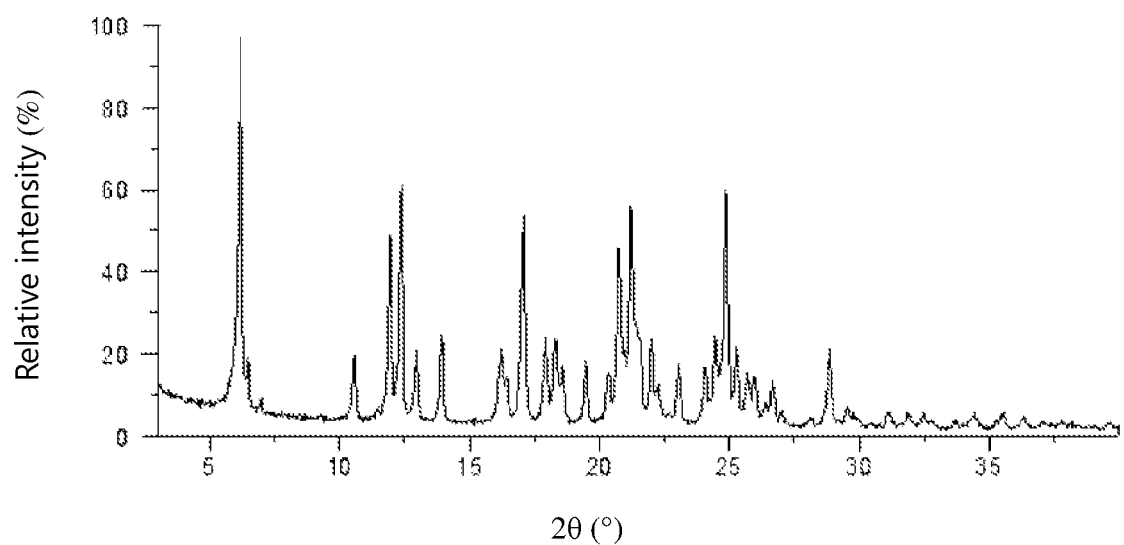
FIG. 4 is a XRPD pattern of the crystal form B of the compound of formula (II-2).
Figure 5:
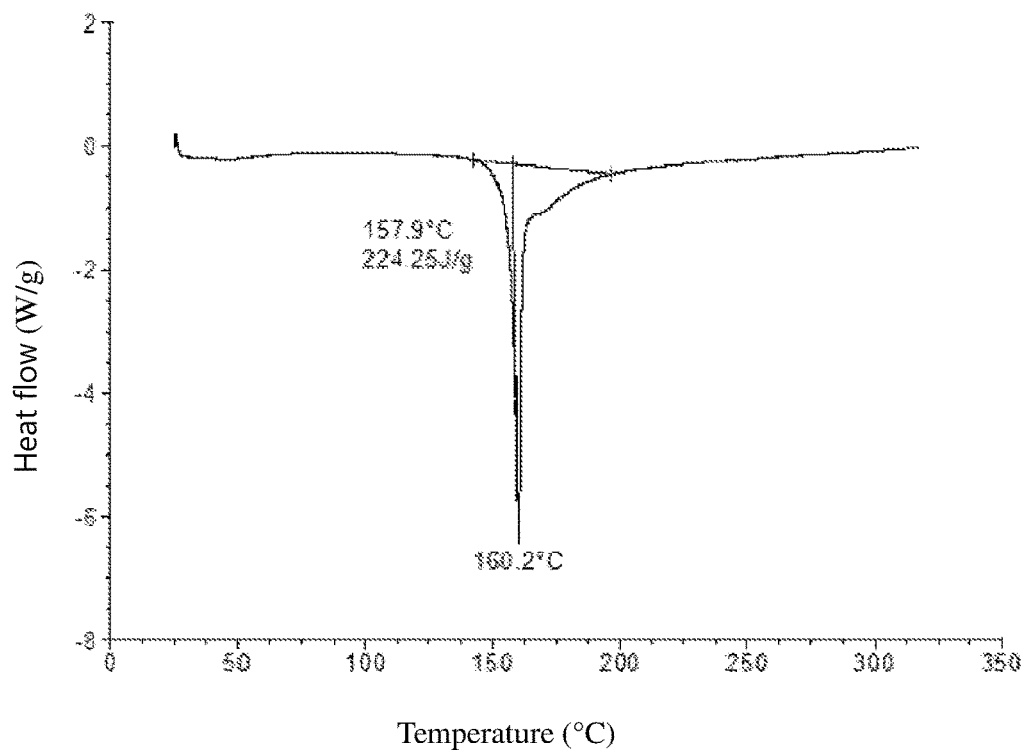
FIG. 5 is a DSC pattern of the crystal form B of the compound of formula (II-2).
Figure 6:
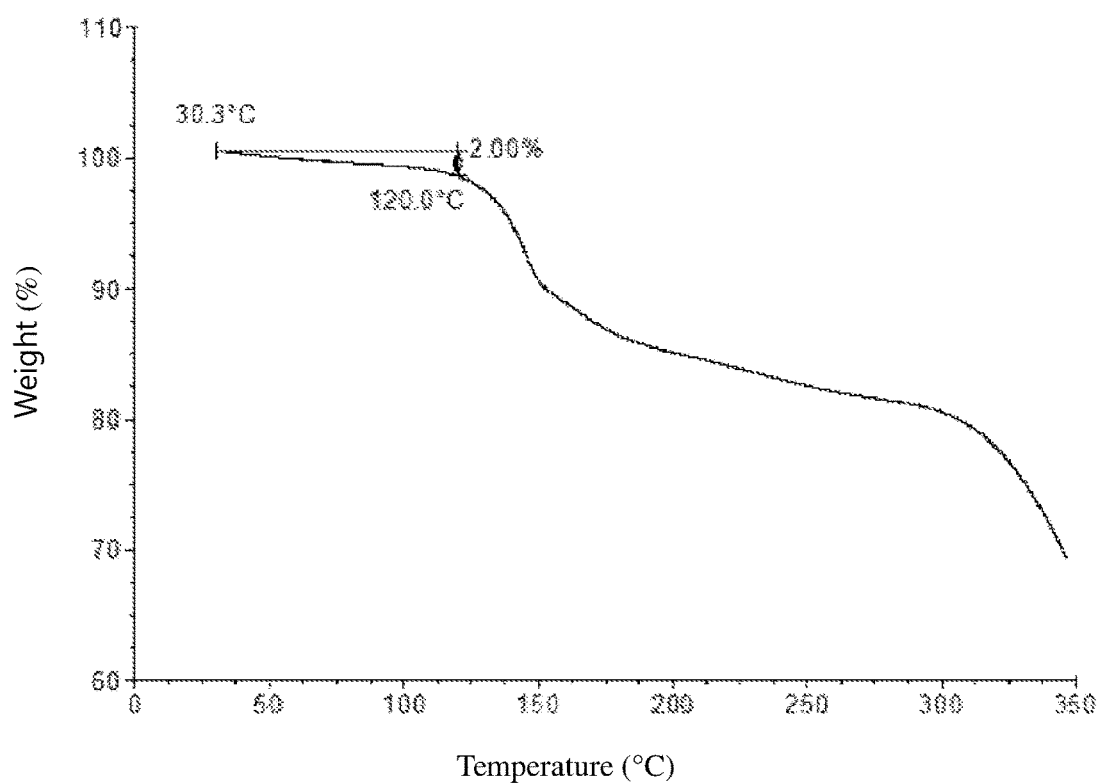
FIG. 6 is a TGA pattern of the crystal form B of the compound of formula (II-2).

11. The crystal form B as defined in claim 9, wherein, the X-ray powder diffraction pattern thereof is shown in FIG. 4.

12. A preparation method of the crystal form B as defined in claim 8, comprising the following steps:
  1) dissolving a compound of formula (I) in an organic solvent, then adding acetic acid and stirring;
  2) filtering under reduced pressure, collecting filter cake;
  3) vacuum drying the filter cake.

13. The preparation method as defined in claim 12, wherein, the organic solvent is ethyl acetate.

* * * * *